United States Patent
Chen et al.

(10) Patent No.: US 7,410,783 B2
(45) Date of Patent: Aug. 12, 2008

(54) METHOD FOR PRODUCING BIODEGRADABLE POLYESTER

(75) Inventors: C. Will Chen, Taipei (TW); Ting-Yen Huang, Taichung (TW); Trong-Ming Don, Danshuei Township, Taipei County (TW)

(73) Assignee: Tatung University, Taipei (TW)

( * ) Notice: Subject to any disclaimer, the term of this patent is extended or adjusted under 35 U.S.C. 154(b) by 329 days.

(21) Appl. No.: 11/432,354

(22) Filed: May 12, 2006

(65) Prior Publication Data

US 2007/0264696 A1 Nov. 15, 2007

(51) Int. Cl.
*C12P 7/62* (2006.01)
(52) U.S. Cl. ...................................... 435/135
(58) Field of Classification Search ........................ None
See application file for complete search history.

(56) References Cited

U.S. PATENT DOCUMENTS

| | | | | |
|---|---|---|---|---|
| 5,229,279 A | * | 7/1993 | Peoples et al. | 435/135 |
| 5,245,023 A | * | 9/1993 | Peoples et al. | 536/23.2 |
| 5,401,657 A | * | 3/1995 | Jones et al. | 435/252.1 |
| 5,663,063 A | * | 9/1997 | Peoples et al. | 435/135 |
| 5,858,748 A | * | 1/1999 | Jones et al. | 435/183 |

* cited by examiner

*Primary Examiner*—Herbert J Lilling
(74) *Attorney, Agent, or Firm*—Bacon & Thomas, PLLC.

(57) ABSTRACT

The present invention relates to a method to produce biodegradable polyester, which comprises the following steps: (a) mixing a carbon source, a nitrogen source and water into a reactive material to perform pretreatment; (b) providing a halophilic *bacterium*, a starting broth and culture with the reactive material; (c) feeding the reactive material; and (d) extracting the polyester from the fermentation broth; wherein, the *bacterium* has a salt tolerance of 10-30%.

14 Claims, 4 Drawing Sheets

METHOD FOR PRODUCING BIODEGRADABLE POLYESTER

BACKGROUND OF THE INVENTION

1. Field of the Invention

The present invention relates to a method for producing polyester, particularly biodegradable polyester.

2. Description of Related Art

In view of the environmental problems caused by non-degradable plastics discarded in farms, landfills, rivers and oceans, the plastics industry is devoted to the research and development of environment-friendly products which can be degraded by natural life. Microbial polyester is suitable not only to be made into environment-friendly products but also biodegradable plastic bottles, wrapping films, or water-proof films for fibers, papers or cards (serving as substitutes of non-degradable polyethylene or aluminum films), while it can also be utilized in the fields of biomedicine such as the manufacture of bone plates, bone nails, drug delivery or cell proliferation vehicles so as to achieve the purpose of degradation by life in a natural environment.

Though it was discovered in 1920s that microbes are capable of fermenting and generating microbial polyester using natural carbon sources, the production cost has been high due to a technical bottleneck in mass production, consequently preventing it from further uses. A number of techniques have been made in attempts to produce microbial polyester in large amounts, including transforming carbon source materials by natural bacteria strains so as to proceed with fermenting and producing microbial polyester. However, because of the common problems of contamination by undesirable strains during the culture of natural strains, complicated controlling strategies like limiting nitrogen sources, phosphorous sources or dissolved oxygen must be taken for high concentration of microbial polyester to be obtained. Thus, continuous fermentation cannot be employed, and the efficiency of mass production is limited. Besides, transgenic strains are also employed to transform carbon sources into microbial polyester, mainly by taking advantages of the rapid proliferation of microbes, such as *E. coli*, to proceed with mass production. However, transgenic strains must undergo a certain induction process upon expression of exogenous genes, and materials influencing gene expression must be removed from the media, making the costs of fermentation even higher, continuous fermentation impossible, and the efficiency poor in industrial scale uses.

Furthermore, the concentration of the microbial polyester is very low, which is produced by strains capable of utilizing phenol compounds that are not usable to other general microbes, or by salt-resistant strains that transform glucose or dissolvable starch. Thus, the process must be improved before it can be applied to industry-scale mass production.

SUMMARY OF THE INVENTION

The present invention takes the advantage of the properties of natural halobacteria strains to extrude low-cost rice bran or wheat bran together with a starch mixture. The resulting concentration and production efficiency of microbial polyester product is far higher than that of prior art. The present invention does not need the induction process of transgenic strains, and it is capable of large-scale production by using semi-continuous or continuous feeding fermentation.

The present invention relates to a method of producing biodegradable polyester, including the following steps: (a) mixing a carbon source, a nitrogen source and water into a reactive mixture to perform pretreatment; (b) mixing a halophilic *bacterium*, a starting broth, and the reactive mixture together to form reactive material, and culture the reactive material for fermentation; (c) feeding the reactive material; and (d) extracting the polyester from the fermented broth; wherein, the *bacterium* has salt tolerance of 10-30%.

The carbon source in step (a) can be any kind carbon source known in the art. Preferably, the carbon source is selected from a group consisting of: cassava starch, cornstarch, potato starch, grass family starch, pulse family starch, wheat starch, rice bran, wheat bran, glucose, and molasses. The nitrogen source can be any kind nitrogen source known in the art. Preferably at least one nitrogen source is selected from a group consisting of: yeast extracts, soy bean extracts, ammonium sulfate, and whey. The pretreatment in step (a) refers to the degradation reaction of contents of the mixture, including mechanic degradation or enzymatic digestion, mainly for degrading macromolecules in starch so as to be used by microbes; the degradation reactions are preferable to be performed through amylase in order to react with starch and proceed with more efficient degradation. Alternatively, a high-temperature, high-pressure extruder can be used in the treatment such that the macromolecules in starch, rice bran or wheat bran are degraded and able to be used by microbes. To improve the efficiency of the hydrolysis reactions in the pretreatment of the starch mixture, a suitable amount of amylase can be added. The desired amylase can be any amylase known in the art but preferably is: plant α-amylase, microbial α-amylase, β-amylase, isoamylase, glucoamylase, pullulanase, Cyclodextrin Glucanotransferase, β-fructofuranosidase, glucoisomerase. The extruder used in the present invention can be any extruder known in the art but preferably is a single-screw extruder.

The halobacteria in step (b) can be any halobacteria known in the art but preferably is *Haloferax mediterranei*. In step (b), the controlling conditions include any factor known in the art, such as pH-stat, dissolved oxygen-stat, redox potential-stat, or conductivity-stat, wherein the conductivity is the criteria for adjusting salt concentration in the reaction solution. To optimize fermentation, the range of conductivity is preferably controlled between 2.5-4 S/m; when the fermentation solution is at pH 6.5-7.5, step (c) is performed to feed reactive materials and replenish consumed carbon source and nitrogen source. The reactive materials in this step comprise carbon source, nitrogen source and salt, used to adjust the environment of fermentation to the one suitable for growth of halobacteria.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
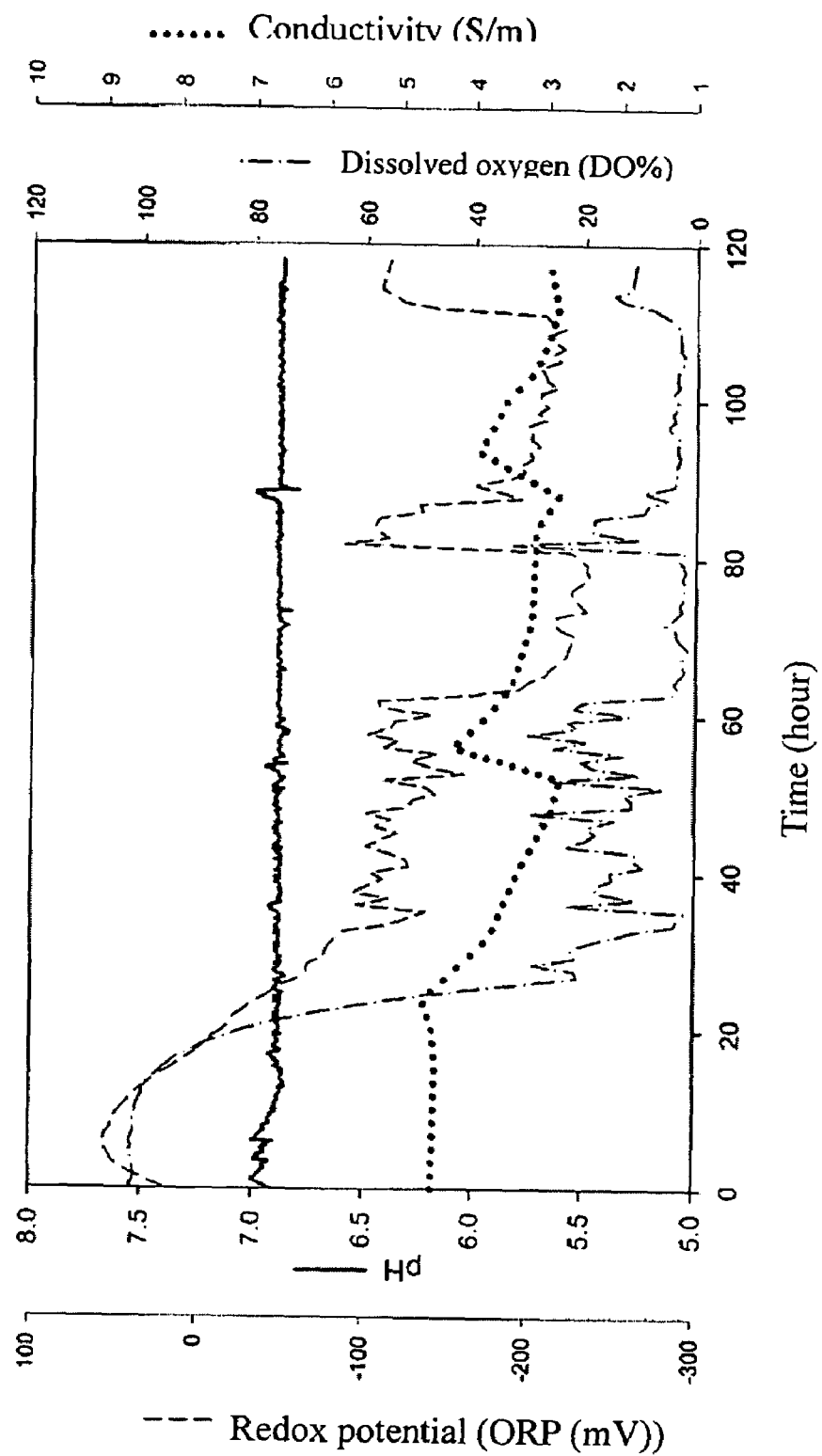
FIG. 1 illustrates changes in various factors in the environment of fermentation in Example 1.

To improve efficiency of the method in the present invention, a pretreatment is performed prior to proceeding with the method of the present invention for producing microbial polyester. Starch mixtures for preparation of microbial polyester are fed into a single-screw extruder (purchased from Yea Jing Mechanics, Taipei, Taiwan), and starch mixtures are degraded under high temperature and high pressure inside the extruder (in the examples of the present invention, four stages of heating are set: first stage 50-60° C., second stage 60-70° C., third stage 70-90° C., fourth stage 85-105° C.), so that the starch mixtures are degraded and the contents are more easily utilized by halobacteria. The resulting mixture is ground by a high-speed pulverizer. Pulverized powder is used as the starting medium and feeding materials in the fermentation process.

In the examples of the present invention, the fermentation process is performed in conjunction with automatic control software, collecting data and controlling process in the course of fermentation by high-throughput data retrieval and a control card PCL-818L (Advantech, Taiwan). Two daughter boards are connected thereto, wherein wiring terminal board PCL-8115 is responsible for receiving online signals, and power relay board PCL-885 is used to control the feeding motor. Meanwhile, graphic control software Genie 3.0 (Advantech) is used as the surveillance software during fermentation culture. The signals received by a detector are converted to analog signals by an A/D converter, transmitted back to a computer, and controlled by the surveillance software in the computer in coordination with a timer to control the electromagnetic valve and the motor switch, so that the purpose of control is achieved.

EXAMPLE 1

The fermentation broth having contents comprising: sodium chloride 234 g/l, sodium bicarbonate 0.2 g/l, sodium bromide 0.5 g/l, magnesium sulfate 30 g/l, magnesium chloride 19.5 g/l, calcium chloride 1 g/l, potassium chloride 5 g/l, yeast extract 7.5 g/l is prepared, and has added thereto an extruded starch mixture (containing weight ratio of rice bran and corn starch of 1:8) serving as a carbon source, resulting in a starting broth.

*Haloferax mediterranei* is cultivated in a 250 ml culture; after 36 hours, the culture liquid is inoculated in a 5 L fermentation tank (CMBS Model CMF-5, FIRSTEK, Taiwan) containing 2.5 L starting broth and fermented for 118 hours. The 5 L fermentation tank is equipped with a pH regulator (Suntex PC330, Ingold pH electrode), which is used to proceed with pH-stat feeding control, and a DO controller responsible for controlling dissolved oxygen. During the initial stages of fermentation, air is delivered into the tank by an air pump at a flow rate of 6 L/min to facilitate growth of bacteria.

At the beginning of fermentation, the pH value decreases due to the carbon source depletion, but it can be maintained at 6.8 or above by adding 10N sodium hydroxide. Once the carbon source is consumed to a low concentration by halobacteria, the pH value of the fermentation liquid increases; when it rises to 7.0 (6.9-7.1), reactive materials are fed to replenish carbon and nitrogen source. The feeding reactive materials comprise extruded starch mixture 50 g/L and yeast extract 85 g/L. When the fermentation liquid reaches 4.5 L, 2 L is taken out and the remaining fermentation liquid is added with an appropriate amount of salt to maintain salt concentration, which is left in the fermentation tank as a seed and continues to ferment.

Referring to FIG. 1, in which changes of the factors in the entire fermentation environment are illustrated and can be used as the criteria of replenishing reactive materials, it can be seen that the pH value is controlled around 6.9, and conductivity serving as the criteria of replenishing salt dropped to 3 S/m when fermentation was proceeded for 53.5 and 91.5 hours. At these moments, salts were added to increase conductivity to 4 S/m.

Figure 2:
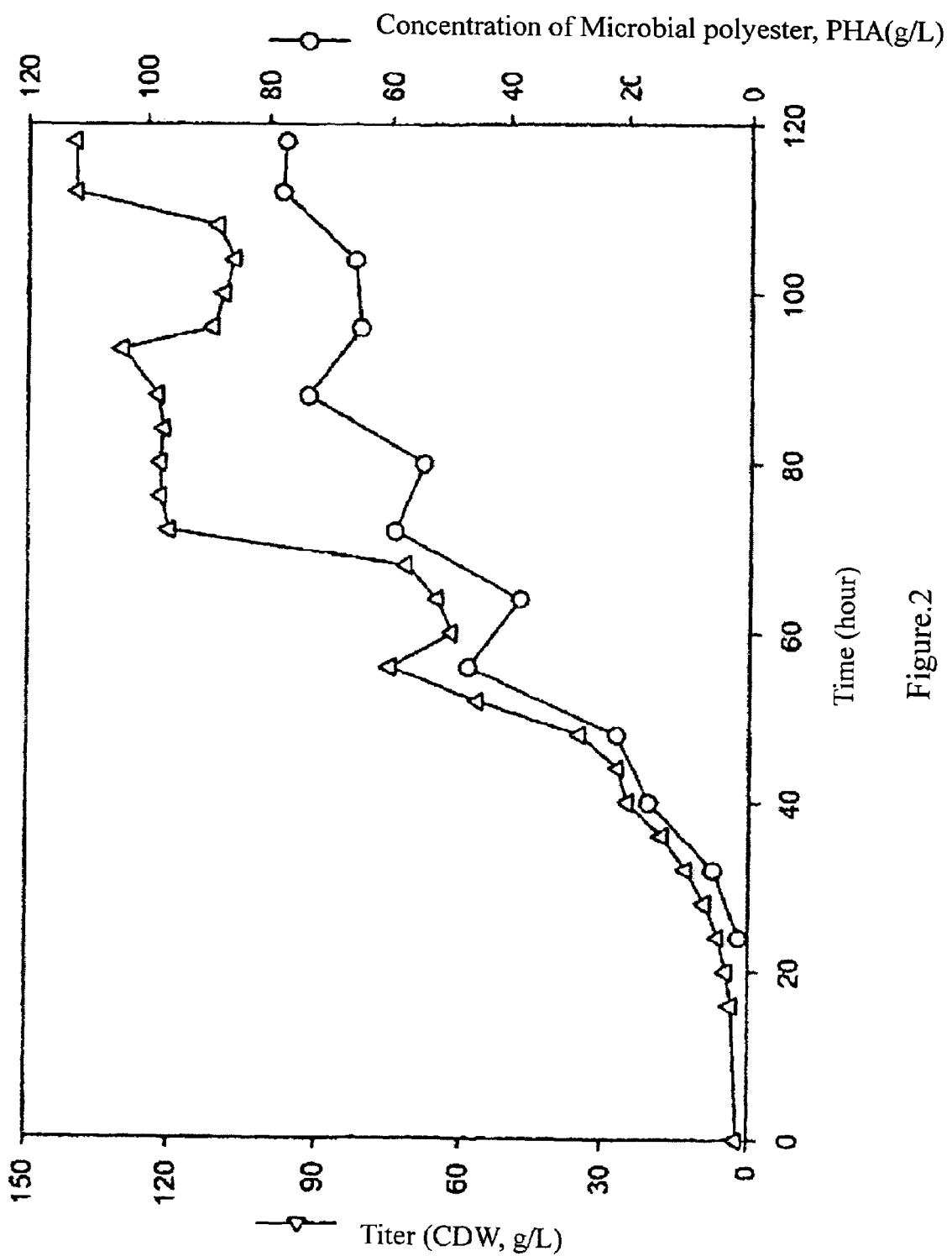
FIG. 2 illustrates changes in titer and production of microbial polyester in Example 1.

Referring to FIG. 2, the titer of *Haloferax mediterranei* used in this example was not changed during the first 24 hours of fermentation, but when fermentation was performed for 24-26 hours, a log phase was reached so that the titer rose rapidly from 6.1 g/L to 75.1 g/L. Reactive materials were fed at $17^{th}$ hour, and the 4.5 L-limit was reached when fermentation had been proceeded for 53.5 hours. Thus, 2 L fermentation liquid was taken out, and the remaining fermentation liquid was added with salts depending on conductivity. Because the fermentation environment was changed, the titer of the bacteria was reduced to 62.1 g/L; but by replenishing the carbon source and the nitrogen source, bacteria began rapid proliferation, so the cell concentration could reach 130.1 g/L when fermentation had been proceeded for 93.5 hours.

At the 93.5 hour of fermentation, fermentation liquid was taken out again thus causing the titer of bacteria reduced to 106.9 g/L, however it reached 140 g/L at the end of the $118^{th}$ hour of further fermentation.

On the changes in produced microbial polyester, referring to FIG. 2, the cultured bacteria began producing microbial polyester rapidly, with the concentration drastically raised from 1.6 g/L to 73.6 g/L, but the producing rate of microbial polyester slowed down thereafter. At the end of fermentation, the maximum concentration of microbial polyester reached 78 g/L.

In the course of fermentation, the need for oxygen increased with growth of cultured bacteria, while dissolved oxygen (DO) decreased along therewith. When DO approached 20%, the electromagnetic valve was activated, and the intervals of feeding pure oxygen were controlled by the surveillance software.

EXAMPLE 2

Extruded corn starch was used as the carbon source in the example, and the steps of fermentation were roughly the same as those of Example 1. Time needed for the entire fermentation process was 88 hours in total.

Conductivity was reduced to 3 S/m at $40^{th}$ and $73.5^{th}$ hour in the course of fermentation, and then salts were added to make conductivity increase to 4 S/m.

During the first 16 hours of fermentation, the titer did not vary significantly. However, the bacteria population entered a log phase during 16-40 hours of fermentation, so the titer rose from 5 g/L to 32 g/L. The feeding reactive materials comprise extruded cornstarch 50 g/L and yeast extract 85 g/L. Reactive materials were fed at $11.5^{th}$ hour, and the volume reached the 4.5 L upper limit. Therefore, 2 L fermentation liquid was taken out and the salts were added to the remaining fermentation liquid depending on the changes in conductivity. Because the environment of fermentation had been altered, the titer was reduced, but bacteria resumed rapid growing upon replenishment of carbon source and nitrogen source. At $72^{nd}$ hour, the titer reached up to 58 g/L.

At 73.5 hour of fermentation, fermentation liquid was taken out for the second time, while the titer was consequently reduced to 47 g/L. Fermentation was carried on to 80 hours, and the titer was raised again, up to 62.6 g/L at the end of $88^{th}$ hour.

On the changes in the amount of produced microbial polyester, the cultured bacteria rapidly produced microbial polyester during 20-40 hours of fermentation, with the level raised from 1.8 g/L to 17.4 g/L. Microbial polyester was produced at a slower rate thereafter, while the concentration of microbial polyester was maintained at around 20 g/L. At the $72^{nd}$ hour of fermentation, the maximum concentration of microbial polyester could reach up to 26.6 g/L.

EXAMPLES 3 AND 4

Fermentation was conducted according to the procedures in Example 1, except that the carbon source was changed. The carbon source of Example 3 was extruded wheat bran and cornstarch (1:2), and the carbon source of Example 4 was solely glucose. The experimental results of Examples 1 to 4 are illustrated in Table 1.

Table 1 shows titers and concentrations of microbial polyester after fermentation using different carbon sources.

| Carbon source | Maximum titer (g/L) | Microbial polyester concentration (g/L) | Weight percentage of microbial polyester to bacteria body (wt %) |
|---|---|---|---|
| Extruded rice bran and cornstarch (Example 1) | 140.0 | 78 | 55.7 |
| Extruded corn starch (Example 2) | 62.6 | 24.2 | 38.7 |
| Extruded wheat bran and cornstarch (Example 3) | 131.0 | 52.7 | 40.2 |
| Glucose (Example 4) | 85.8 | 23.0 | 26.8 |

From the above results, it is concluded that using the method of the present invention and employing extruded agricultural materials as the carbon sources to produce microbial polyester result in higher production than that of prior arts. Besides, cautions must be taken in the combination of process and automatic equipment during prior art mass production, while the present invention takes advantages of variations in environmental factors and to feed extruded materials and replenish salts, requiring only control of automatic equipment and thereby possesses excellent industrial applicability.

Figure 3:
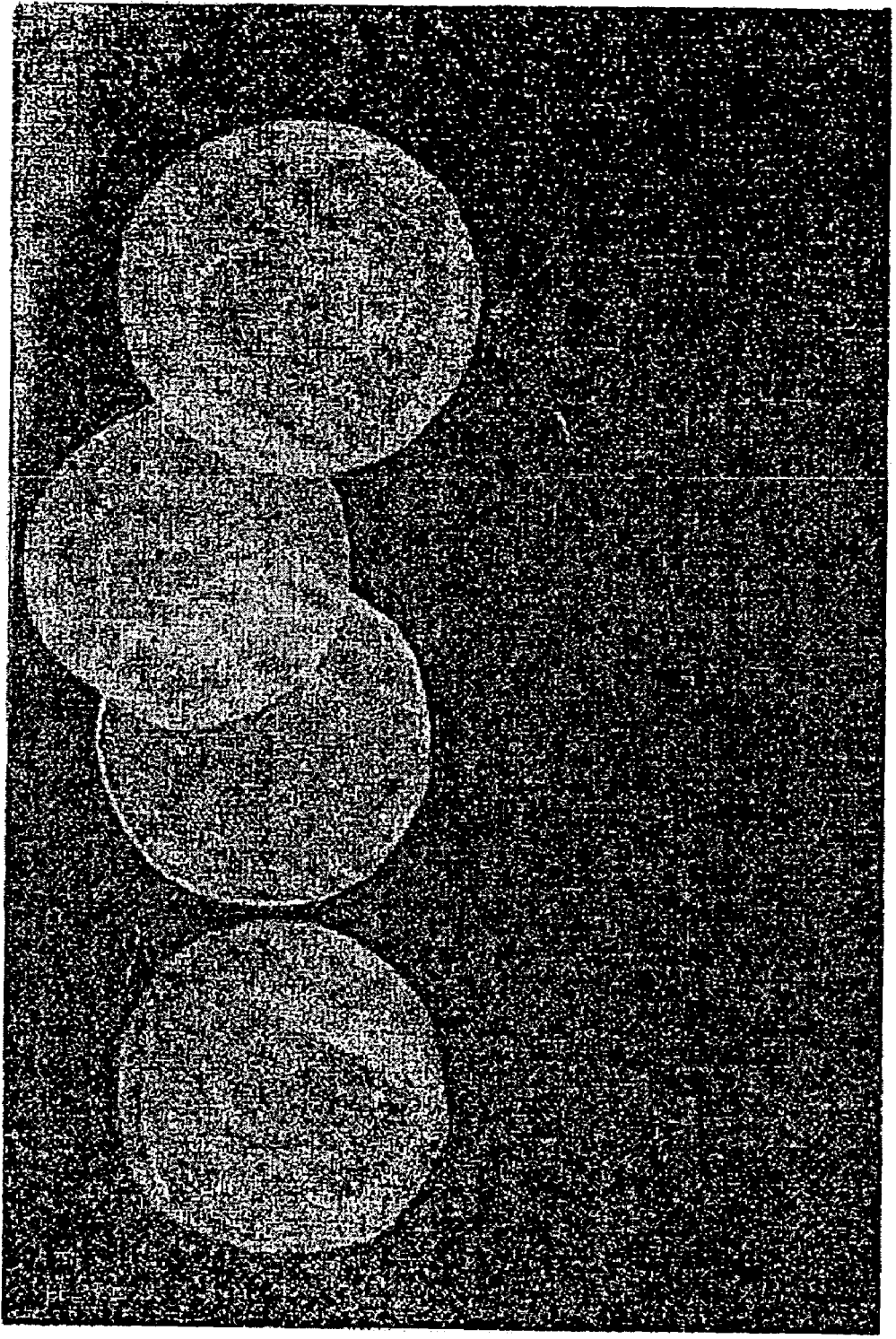
FIG. 3 shows the microbial polyester films prepared by the method of the present invention.

The method for extraction and quantification of microbial polyester is as follows: 100 ml of the culture liquid is centrifuged, the supernatant is discarded, and the bacteria bodies are treated with a freeze dryer and ground into powder. Microbial polyester is extracted from 2.5 g dried bacteria bodies using a Soxhlet extractor with 250 ml chloroform under 90° C. for 6 hours. The chloroform solvent is recovered from the extract in a rotary vacuum evaporator, where microbial polyester film is thus obtained. See FIG. 3.

Figure 4:
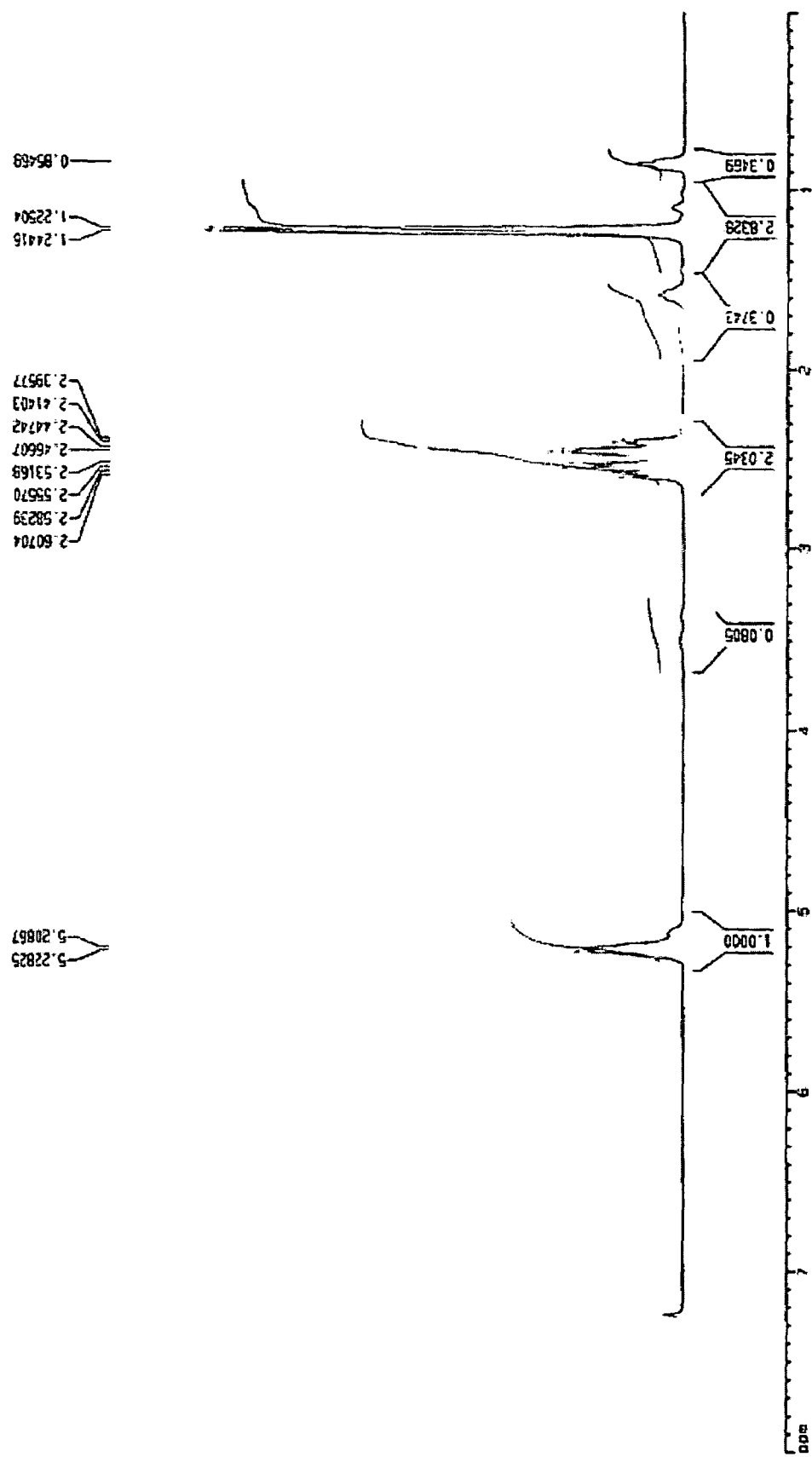
FIG. 4 is the $^1$H-NMR spectrum of microbial polyester prepared by the method of the present invention.

Microbial polyester prepared by the method of the present invention is identified by $^1$H-NMR. The structure of the microbial polyester is a polyester polymer: polyhydroxyalkanoates (PHA). See FIG. 4.

Natural halobacteria are utilized to transform cheap agricultural products and proceed with fermentation to generate microbial polyester. The maximum production can reach up to 78 g/L, which is far higher than the concentration of microbial polyester generated in extreme environments reported by various institutes to date. In addition, ongoing semi-continuous fermentative production is also possible. Transgenic strains are not used in the present invention, so the expensive and inefficient process of start-up, gene induction, product recovery, down time, clearing, and resuming fermentation is avoided. Besides, a pH-stat controlling method that is easy to be monitored is used, allowing it to be applied to regular fermentation plants and helps reduce the costs of operation of fermentation.

Although the present invention has been explained in relation to its preferred embodiment, it is to be understood that many other possible modifications and variations can be made without departing from the scope of the invention as hereinafter claimed.

What is claimed is:

1. A method for producing biodegradable polyester, comprising steps of:
    (a) mixing a carbon source, a nitrogen source and water into a reactive mixture to perform pretreatment;
    (b) mixing a halophilic *bacterium*, a starting broth, and the reactive mixture together to form a reactive material, and culture the reactive material for fermentation;
    (c) feeding the reactive material; and
    (d) extracting the polyester from the fermented broth;
wherein the *bacterium* has salt tolerance of 10-30%.

2. The method of claim 1, wherein the carbon source of step (a) is at least one selected from a group consisting of: cassava starch, cornstarch, potato starch, grass family starch, pulse family starch, wheat starch, rice bran, wheat bran, glucose, and molasses.

3. The method of claim 1, wherein the nitrogen source of step (a) is at least one selected from a group consisting of: yeast extracts, soy bean extracts, ammonium sulfate, and whey.

4. The method of claim 1, wherein the pretreatment in step (a) refers to the degradation reaction of contents of the mixture.

5. The method of claim 4, wherein the degradation reaction refers to treatment by amylase and an extruder.

6. The method of claim 5, wherein the amylase is selected from a group consisting of: plant α-amylase, microbial α-amylase, β-amylase, isoamylase, glucoamylase, pullulanase, cyclodextrin glucanotransferase, β-fructofuranosidase, and glucoisomerase.

7. The method of claim 6, wherein the temperature range in which the amylases function is 25-110° C.

8. The method of claim 5, wherein the extruder is a single-screw extruder.

9. The method of claim 1, wherein the halobacteria in step (b) is *Haloferax, Halobacterium, Haloarcula* or *Halococcus*.

10. The method of claim 9, wherein the halobacteria in step (b) is *Haloferax mediterranei*.

11. The method of claim 1, wherein conductivity in step (b) is controlled in order to adjust salt concentration in the reaction liquid.

12. The method of claim 11, wherein the range of conductivity is 2-4 S/m.

13. The method of claim 1, when pH value is between 6.5-7.5, step (b) is performed.

14. The method of claim 1, wherein the fed reactive materials comprise a carbon source, a nitrogen source, and salts.

* * * * *